United States Patent
Assmann et al.

[11] Patent Number: 6,136,830
[45] Date of Patent: Oct. 24, 2000

[54] SULPHONYLOXADIAZOLONES AND THEIR USE AS MICROBICIDES

[75] Inventors: Lutz Assmann, St. Peter-Ording; Peter Gerdes, Aachen; Klaus Stenzel, Düsseldorf, all of Germany

[73] Assignee: Bayer Aktiengesellschaft, Leverkusen, Germany

[21] Appl. No.: 09/402,990

[22] PCT Filed: Apr. 6, 1998

[86] PCT No.: PCT/EP98/01989

§ 371 Date: Oct. 13, 1999

§ 102(e) Date: Oct. 13, 1999

[87] PCT Pub. No.: WO98/47897

PCT Pub. Date: Oct. 29, 1998

[30] Foreign Application Priority Data

Apr. 18, 1997 [DE] Germany .......................... 197 16 258

[51] Int. Cl.[7] ...................... C07D 413/12; A01N 43/836
[52] U.S. Cl. ............................. 514/364; 548/132
[58] Field of Search .............................. 548/132; 514/364

[56] References Cited

U.S. PATENT DOCUMENTS 3,994,909 11/1976 Pommer et al. .................... 260/302 D
4,420,486 12/1983 Ohyama et al. ........................ 424/272

OTHER PUBLICATIONS

Database WPI, Section Ch, Week 8722, Derwent Pulications Ltd., London, GB; Class C02, AN 87–154900, XP002073605, –&JP 62 093 283 A (Idemitsu Kosan Co Ltd), siehe Zusammenfassung.

*Primary Examiner*—Robert Gerstl
*Attorney, Agent, or Firm*—Joseph C. Gil

[57] ABSTRACT

Novel sulphonyloxadiazolones of the formula

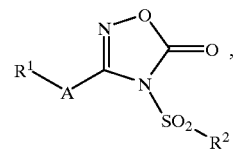

(I)

in which

A represents oxygen, sulphur, —SO—, —SO$_2$— or

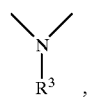

where

R$^3$ represents hydrogen or alkyl,

R$^1$ represents optionally substituted cycloalkyl, optionally substituted cycloalkenyl or optionally substituted aryl and R$^2$ represents optionally substituted heterocyclyl, a process for preparing these substances and their use as microbicides in crop protection and in the protection of materials.

8 Claims, No Drawings

SULPHONYLOXADIAZOLONES AND THEIR USE AS MICROBICIDES

The present invention relates to novel sulphonyloxadiazolones, to a process for their preparation and to their use as microbicides in crop protection and in the protection of materials.

Certain sulphonyloxadiazolones, such as, for example, 4-[(4-chlorophenyl)-sulphonyl]-3-(2,4,6-trimethylphenyl)-1,2,4-oxadiazol-5(4H)-one, are already known (cf. Zh. Org. Khim. 27 (1991), 1262–70). A biological action of these compounds has hitherto not been described.

This invention, accordingly, provides novel sulphonyloxadiazolones of the formula

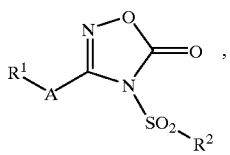
(I)

in which

A represents oxygen, sulphur, —SO—, —SO$_2$— or

where

R$^3$ represents hydrogen or alkyl,

R$^1$ represents optionally substituted cycloalkyl, optionally substituted cycloalkenyl or optionally substituted aryl and R$^2$ represents optionally substituted heterocyclyl.

Furthermore, it has been found that sulphonyloxadiazolones of the formula (I) are obtained when oxadiazolones of the formula

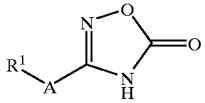
(II)

in which

A and R$^1$ are as defined above, are reacted with sulphonyl halides of the formula

R$^2$—SO$_2$—X (III)

in which

R$^2$ is as defined above and

X represents halogen, if appropriate in the presence of an acid binder and if appropriate in the presence of a diluent.

Finally, it has been found that the sulphonyloxadiazolones of the formula (I) have very good microbicidal properties and can be used both in crop protection and in the protection of materials.

Surprisingly, the sulphonyloxadiazolones of the formula (I) according to the invention exhibit better activity against undesirable microorganisms, in particular fungi, than the constitutionally most similar prior-art compounds of the same direction of action.

The formula (I) provides a general definition of the substances according to the invention.

A also preferably represents oxygen, sulphur, —SO—, —SO$_2$— or

R$^3$ preferably represents hydrogen or alkyl having 1 to 4 carbon atoms.

R$^1$ preferably represents cycloalkenyl having 3 to 8 carbon atoms or cycloalkyl having 3 to 8 carbon atoms which is optionally mono- to trisubstituted by identical or different substituents from the group consisting of halogen and alkyl having 1 to 3 carbon atoms.

R$^1$ furthermore preferably represents aryl having 6 to 10 carbon atoms, where each of these radicals may be mono- to trisubstituted by identical or different substituents from the group consisting of halogen, nitro, carbamoyl;

in each case straight-chain or branched alkyl, alkoxy, alkylthio or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio or halogenoalkylsulphonyl having in each case 1 to 6 carbon atoms and 1 to 5 identical or different halogen atoms;

in each case straight-chain or branched halogenoalkenyl or halogenoalkenyloxy having in each case 2 to 6 carbon atoms and 1 to 5 identical or different halogen atoms;

in each case straight-chain or branched alkylamino, dialkylamino, alkylcarbonyl, alkoxycarbonyl, hydroximinoalkyl or alkoximinoalkyl having in each case 1 to 6 carbon atoms in the individual alkyl moieties;

in each case doubly attached alkylene or dioxyalkylene having in each case 1 to 6 carbon atoms and being in each case optionally mono- to tetrasubstituted by identical or different substituents from the group consisting of halogen, straight-chain or branched alkyl having 1 to 4 carbon atoms and straight-chain or branched halogenoalkyl having 1 to 4 carbon atoms and 1 to 5 identical or different halogen atoms;

cycloalkyl having 3 to 6 carbon atoms; and/or aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, where these aromatic or heterocyclic radicals may be mono- to trisubstituted by identical or different substituents from the group consisting of halogen, nitro, straight-chain or branched alkyl having 1 to 4 carbon atoms, straight-chain or branched halogenoalkyl having 1 to 4 carbon atoms and 1 to 5 identical or different halogen atoms, straight-chain or branched alkoxy or alkylthio having 1 to 4 carbon atoms, and by straight-chain or branched halogenoalkoxy having 1 to 4 carbon atoms and 1 to 9 identical or different halogen atoms.

$R^2$ preferably represents a heterocyclyl radical having 5 or 6 ring members and 1 to 3 heteroatoms, such as nitrogen, oxygen and/or, where this radical may be mono- to trisubstituted by identical or different substituents from the group consisting of halogen, cyano, nitro, amino, hydroxyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkylcarbonyl having 1 to 4 carbon atoms in the alkyl moiety, alkoxycarbonyl having 1 to 3 carbon atoms in the alkoxy moiety, carbamoyl, alkyaminocarbonyl having 1 to 4 carbon atoms in the alkyl moiety, dialkylaminocarbonyl having 1 to 4 carbon atoms in the individual alkyl moieties, hydroximinoalkyl or alkoximinoalkyl having in each case 1 to 4 carbon atoms in the individual alkyl moieties and cycloalkyl having 3 to 6 carbon atoms.

Heterocyclyl represents cyclic compounds in which at least one ring member is a heteroatom, i.e. an atom different from carbon. If the ring contains a plurality of heteroatoms, these can be identical or different. Preferred heteroatoms are oxygen, nitrogen or sulphur. If the ring contains a plurality of oxygen atoms, these are not adjacent.

A also particularly preferably represents oxygen, sulphur, —SO—, —SO$_2$— or

$R^3$ particularly preferably represents hydrogen or methyl.

$R^1$ particularly preferably represents cyclopropyl, cyclobutyl, cyclopentyl, cyclohexyl, cyclopentenyl or cyclohexenyl, each of which is optionally mono- to trisubstituted by chlorine, methyl, ethyl, n- or i-propyl.

$R^1$ also particularly preferably represents phenyl which may be mono- to trisubstituted by identical or different substituents from the group consisting of
fluorine, chlorine, bromine, nitro, carbamoyl, methyl, ethyl, n- or i-propyl, n-, i-, s- or t-butyl, methoxy, ethoxy, n- or i-propoxy, methylthio, ethylthio, n- or i-propylthio, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio or trifluoromethylsulphonyl, methylamino, ethylamino, n- or i-propylamino, dimethylamino, diethylamino, acetyl, propionyl, methoxycarbonyl, ethoxycarbonyl, hydroximinomethyl, hydroximinoethyl, methoximinomethyl, ethoximinomethyl, methoximinoethyl or ethoximinoethyl,
in each case doubly attached trimethylene (propane-1,3-diyl), methylenedioxy or ethylenedioxy, which is optionally mono- or tetrasubstituted by identical or different substituents from the group consisting of fluorine, chlorine, methyl and trifluoromethyl,
cyclopropyl, cyclobutyl, cyclopentyl or cyclohexyl, and/or
by phenyl, phenoxy, phenylthio, benzyl, benzyloxy, benzylthio, pyridyl, pyrimidinyl or thienyl, where these radicals may be mono- to trisubstituted by identical or different substituents from the group consisting of
fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy and/or trifluoroethoxy.

$R^2$ particularly preferably represents furyl, thienyl, oxazolyl, isoxazolyl, pyrazolyl, imidazolyl, thiazolyl, isothiazolyl, oxadiazolyl, thiadiazolyl, pyridinyl, pyridazinyl, pyrazinyl, 1,2,3-triazinyl, 1,2,4-triazinyl, 1,3,5-triazinyl, pyrrolidinyl, piperidinyl or morpholinyl, where these radicals may be mono-, di- or trisubstituted by identical or different substituents from the group consisting of fluorine, chlorine, bromine, cyano, nitro, amino, hydroxyl, carbamoyl, methyl, ethyl, n- or i-propyl, n-, i-, s-, or t-butyl, cyclopropyl, methoxy, ethoxy, n- or i-propoxy, trifluoromethyl, trifluoroethyl, difluoromethoxy, trifluoromethoxy, acetyl, propionyl, methoxycarbonyl, ethoxycarbonyl, hydroximinomethyl, hydroximinoethyl, methoximinomethyl, ethoximinomethyl, methoximinoethyl and ethoximinoethyl.

A very particularly preferably represents oxygen.

$R^1$ very particularly preferably represents phenyl which may be mono- or trisubstituted by identical or different substituents from the group consisting of
fluorine, chlorine, bromine, nitro, carbamoyl, methyl, ethyl, n- or i-propyl, n-, i-, s- or t-butyl, methoxy, ethoxy, n- or i-propoxy, methylthio, ethylthio, n- or i-propylthio, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio or trifluoromethylsulphonyl, methylamino, ethylamino, n- or i-propylamino, dimethylamino, diethylamino, acetyl, propionyl, methoxycarbonyl, ethoxycarbonyl, hydroximinomethyl, hydroximinoethyl, methoximinomethyl, ethoximinomethyl, methoximinoethyl or ethoximinoethyl,
in each case doubly attached trimethylene (propane-1,3-diyl), methylenedioxy or ethylenedioxy, which is optionally mono- to tetrasubstituted by identical or different substituents from the group consisting of fluorine, chlorine, methyl and trifluoromethyl,
cyclopropyl, cyclobutyl, cyclopentyl or cyclohexyl, and/or
by phenyl, phenoxy, phenylthio, benzyl, benzyloxy, benzylthio, pyridyl, pyrimidinyl or thienyl, where these radicals may be mono- to trisubstituted by identical or different substituents from the group consisting of
fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy and/or trifluoroethoxy.

$R^2$ very particularly preferably represents imidazolyl, pyrazolyl, isoxazolyl, thienyl or furyl which is optionally mono- or disubstituted by chlorine, bromine, amino, hydroxyl, methyl and/or cyclopropyl.

The abovementioned general or preferred radical definitions apply both to the end products of the formula (I) and also, correspondingly, to the starting materials or intermediates required in each case for the preparation.

Using, for example, 3-phenoxy4H-[1,2,4]oxadiazol-5-one and 3,5-dimethylisoxazole-4-sulphonyl chloride as starting materials, the course of the process according to the invention can be illustrated by the following scheme:

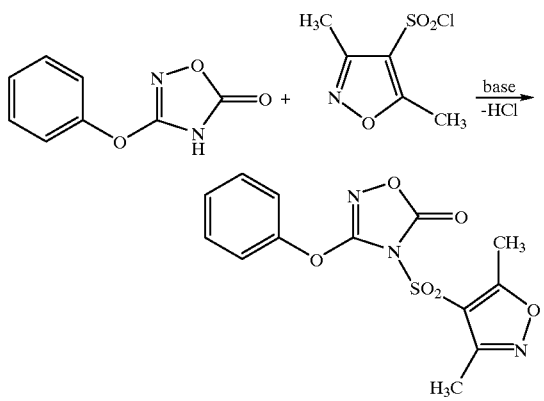

The formula (II) provides a general definition of the oxadiazolones required as starting materials for carrying out the process according to the invention. In this formula, A and $R^1$ preferably or in particular have those meanings which have already been mentioned in connection with the description of the compounds of the formula (I) according to the invention as being preferred or as being particularly preferred for A and $R^1$.

The oxadiazolones of the formula (II) are known or can be prepared by known methods (cf. Chem. Ber. 98, (1965), 144–154)).

The formula (III) provides a general definition of the sulphonyl halides required as reaction components for carrying out the process according to the invention. In this formula, $R^2$ preferably or in particular has the meaning which has already been mentioned in connection with the description of the compounds of the formula (I) according to the invention as being preferred or as being particularly preferred for $R^2$. X preferably represents chlorine.

The sulphonyl halides of the formula (III) are known or can be prepared by known processes (J. Heterocyclic Chem. 1981, 997–1006).

Suitable diluents for carrying out the process according to the invention are all inert organic solvents. Preference is given to using aliphatic, alicyclic or aromatic hydrocarbons, such as petroleum ether, hexane, heptane, cyclohexane, methylcyclohexane, benzene, toluene, xylene or decalene; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methyl isobutyl ketone or cyclohexanone; nitriles, such as acetonitrile, propionitrile, n- or i-butyronitrile or benzonitrile; esters such as methyl acetate or ethyl acetate.

Suitable acid binders for carrying out the process according to the invention are all customary inorganic or organic bases. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide or potassium hydroxide, sodium acetate, potassium acetate, calcium acetate, sodium carbonate, potassium carbonate, potassium bicarbonate or sodium bicarbonate, furthermore ammonium compounds, such as ammonium hydroxide, ammonium acetate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process according to the invention, the reaction temperatures can be varied within a relatively wide range. In general, the process is carried out at temperatures of between 0° C. and 150° C., preferably between 20° C. and 120° C.

For carrying out the process according to the invention, generally 1 to 2 mol, preferably 1 to 1.3 mol, of sulphonyl halide of the formula (III) and, if appropriate, 1.0 to 2.0 mol, preferably 1.0 to 1.3 mol, of acid acceptor are employed per mole of oxadiazolone of the formula (II).

The process according to the invention is generally carried out at atmospheric pressure. However, it is also possible to operate under elevated or reduced pressure—generally between 0.1 bar and 10 bar.

Work-up is carried out by customary methods.

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as. for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*
Sclerotinia species, such as, for example, *Scierotinia scierotiorum;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;* and
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in fruit and vegetable growing and viticulture, such as, for example, against Phytophthora species.

The active compounds according to the invention are also suitable for increasing the yield of crops. Moreover, they have reduced toxicity and are tolerated well by plants.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and boards, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms.

The active compounds according to the invention preferably act against fungi, in particular moulds, wood-discolouring and wood-destroying fungi (Basidiomycetes), and against slime organisms and algae.

Microorganisms of the following genera may be mentioned as examples:
Alternaria, such as *Altemaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Scierophoma, such as *Sclerophoma pityophila,*
Trichoderma, such as *Trichoderma viride,*
Escherichia, such as *Escherichia coli,*
Pseudomonas, such as *Pseudomonas aeruginosa,* and
Staphylococcus, such as *Staphylococcus aureus.*

Depending on their particular physical and/or chemical properties, the active compounds can be converted to the customary formulations, such as solutions, emulsions, suspensions, powders, foams, pastes, granulles, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formnulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorofenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitrol)an, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutnrafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeciam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, toiclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl) ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-2-methyl-4'-trifluoromethoxy-4'-trifluoro-methyl-1,3-thiazole-5-carboxantlide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzanide, 2-(2,3,3-triiodo-2-propenyl)-2H-tetrazole, 2-[(1-methylethyl)sulphony]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-mono-sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyrane-2,1'(3'H)-isobenzofuran]-3'-one, Bactericides:

bromopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

InsecticideslAcaricides/Nematicides:

abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5-(tri-fluoromethyl)-2H-pyrrole-3-carbonitrile, bendiocarb, benfuracarb, bensultap, betacyfluthrin, bifenthrin, BPMC, brofenprox, bromophos A, bufencarb, buprofezin, butocarboxime, butylpyridaben, cadusafos, carbaryl, carbofuran, carbophenothione, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, ometheate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pynrmidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth-promoting substances.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the application rates of active compounds are generally between 0.1 and 10,000 g/ha, preferably between 10 and 1000 g/ha. In the treatment of seed, the application rates of active compounds are generally between 0.001 and 50 g per kilogram of seed, preferably between 0.01 and 10 g per kilogram of seed. In the treatment of the soil, the application rates of active compound are generally between 0.1 and 10,000 g/ha, preferably between 1 and 5000 g/ha.

The compositions used for protecting industrial materials comprise the active compounds generally in an amount of from 1 to 95% by weight, preferably from 10 to 75% by weight.

The use concentrations of the active compounds according to the invention depend on the species and the occurrence of the microorganisms to be controlled, and on the composition of the material to be protected. The optimum rate of application can be determined by test series. The use concentrations are generally in the range from 0.001 to 5% by weight, preferably from 0.05 to 1.0% by weight, based on the material to be protected.

The activity and the activity spectrum of the active compounds to be used according to the invention in the protection of materials, or the compositions, concentrates or quite generally formulations preparable therefrom, can be increased by adding, if appropriate, other antimicrobially active compounds, fungicides, bactericides, herbicides, insecticides or other active compounds for broadening the activity spectrum or obtaining particular effects, such as, for example, the additional protection against insects. These mixtures may have a broader activity spectrum than the compounds according to the invention.

The preparation and use of active compounds according to the invention are illustrated by the following examples.

PREPARATION EXAMPLES
Example 1

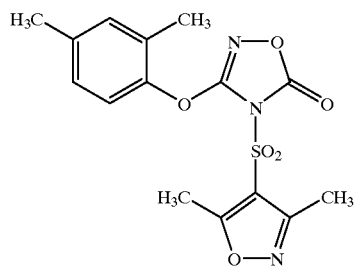

At room temperature, a solution of 0.182 g (0.84 mmol) of 3-(2,4-dimethylphenoxy)-4H-[1,2,4]oxadiazol-5-one and 4 ml of absolute acetonitrile is admixed with stirring with 0.194 g (1.4 mmol) of powdered potassium carbonate, and the mixture is then stirred at room temperature for 10 minutes. Subsequently, 0.17 g (0.84 mmol) of 3,5-dimethylisoxazole-4-sulphonyl chloride is added, and the mixture is stirred at room temperature for another 22 hours. For work-up, the reaction mixture is poured into 20 ml of water. The resulting precipitate is filtered off with suction and washed successively with 5 ml of water and 5 ml of ether. This gives 0.161 g (52% of theory) of 4-(3,5-dimethylisoxazole-4-sulphonyl)-3-(2,4-dimethylphenoxy)-4H-[1.2.4]-oxadiazol-5-one in the form of a solid of melting point 135 to 136° C.

The sulphonyloxadiazolones of the formula (I) listed in Table 1 below are likewise prepared by the abovementioned methods.

TABLE 1

(I)

| Ex. No. | R¹ | A | R² | M. (° C.) | logP |
|---|---|---|---|---|---|
| 2 | 4-methoxycarbonylphenyl | O | 3,5-dimethylisoxazol-4-yl | 157–158 | 3.07 |
| 3 | 2,6-dimethylphenyl | O | 3,5-dimethylisoxazol-4-yl | 143–145 | 3.54 |
| 4 | 2-isopropyl-5 methylphenyl | O | 3,5-dimethylisoxazol-4-yl | 50 | 4.19 |
| 5 | 2,4-dimethylphenyl | O | 3,5-dimethylisoxazol-4-yl |  | 3.63 |

TABLE 1-continued (I)

$$\underset{\underset{SO_2-R^2}{|}}{R^1-A-\overset{N=N}{\underset{N}{\diagdown}}\overset{O}{\diagup}\!\!\!\diagdown}=O$$

| Ex. No. | R¹ | A | R² | M. (° C.) | logP |
|---|---|---|---|---|---|
| 6 | 2-methoxyphenyl | O | 3,4,5-trimethylisoxazole | 168–169 | |
| 7 | 2-tolyl | O | 3,4,5-trimethylisoxazole | | 3.28 |
| 8 | 4-chlorophenyl | O | 3,4,5-trimethylisoxazole | | 3.45 |
| 9 | 3,4-dichlorophenyl | O | 3,4,5-trimethylisoxazole | 130–132 | |
| 10 | 3-tolyl | O | 3,4,5-trimethylisoxazole | 133–135 | |
| 11 | cyclohexylmethyl | N(CH₃)₂ | 3,4,5-trimethylisoxazole | 149–150 | |
| 12 | cyclohexylmethyl | N(CH₃)₂ | 3-amino-4-methyl-5-methylisoxazole | 159–162 | |
| 13 | 2,5-dimethylphenyl | O | 3,4,5-trimethylisoxazole | 161–162 | |
| 14 | 2,5-dimethylphenyl | O | 3-amino-4-methyl-5-methylisoxazole | 181–182 | |

TABLE 1-continued (I)

| Ex. No. | R¹ | A | R² | M. (° C.) | logP |
|---|---|---|---|---|---|
| 15 | 2,6-dimethylphenyl | O | 4-methyl-5-methyl-3-amino-isoxazole | 178–181 | |
| 16 | 3,4-dimethylphenyl | O | 3,4,5-trimethyl-isoxazole | 165–167 | |
| 17 | 3,4-dimethylphenyl | O | 4-methyl-5-methyl-3-amino-isoxazole | 158–160 | |
| 18 | 3,5-dimethylphenyl | O | 3,4,5-trimethyl-isoxazole | 162–163 | |
| 19 | 3,5-dimethylphenyl | O | 4-methyl-5-methyl-3-amino-isoxazole | 207–208 | |
| 20 | 2-methoxyphenyl | O | 4-methyl-5-methyl-3-amino-isoxazole | 168–169 | |
| 21 | 4-methoxyphenyl | O | 3,4,5-trimethyl-isoxazole | 156–158 | |
| 22 | 4-methoxyphenyl | O | 4-methyl-5-methyl-3-amino-isoxazole | 154–155 | |
| 23 | 2,5-dimethylphenyl | O | 4-methyl-5-methyl-3-amino-isoxazole | 171–172 | |

TABLE 1-continued

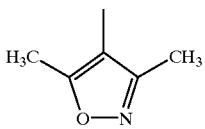

| Ex. No. | R¹ | A | R² | M. (° C.) | logP |
|---|---|---|---|---|---|
| 24 | 4-phenoxyphenyl | O | 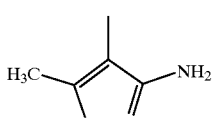 | 158–159 | |
| 25 | 4-phenoxyphenyl | O | 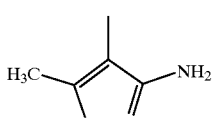 | 159–161 | |

The log P values were determined according to EEC-Directive 79/831 Annex V. A8 by HPLC (gradient method, acetonitrile/0.1% aqueous phosphoric acid).

USE EXAMPLES

Example A
Phytophthora-Test (Tomato)/Protective

| Solvent: | 47 parts by weight of acetone |
|---|---|
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Phytophthora infestans. The plants are then placed in an incubation cabin at approximately 20° C. and 100% relative atmospheric humidity.

Evaluation is carried out 3 days after the inoculation. 0% means an efficacy which corresponds to that of the control, whereas an efficacy of 100% means that no infection is observed.

Active compounds, application rates and test results are shown in the table below.

TABLE A

Phytophthora test (tomato)/protective

| Active compound | Application rate of active compound in g/ha | Efficacy in % |
|---|---|---|
| According to the invention | | |
| 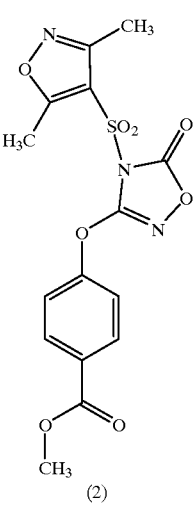 (2) | 50 | 86 |

TABLE A-continued
Phytophthora test (tomato)/protective
| Active compound | Application rate of active compound in g/ha | Efficacy in % |
|---|---|---|
| 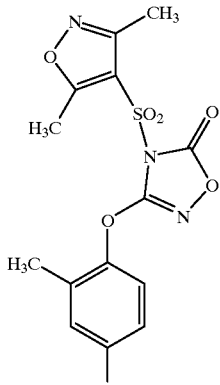 (1) | 50 | 94 |
| 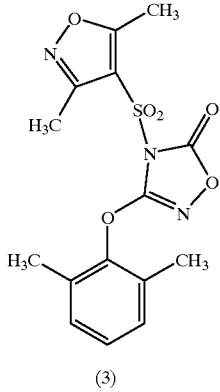 (3) | 50 | 88 |
| 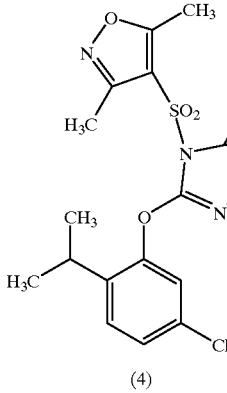 (4) | 50 | 95 |
| 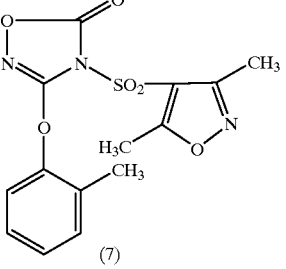 (7) | 50 | 94 |
| 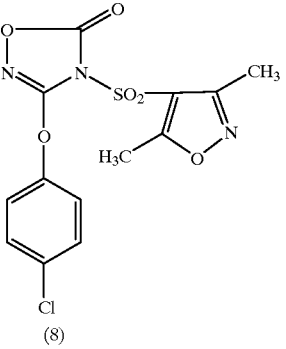 (8) | 50 | 97 |
| 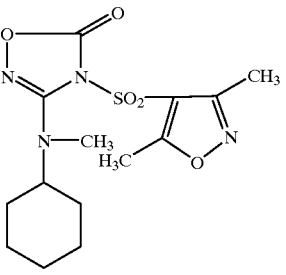 (11) | 50 | 85 |
| 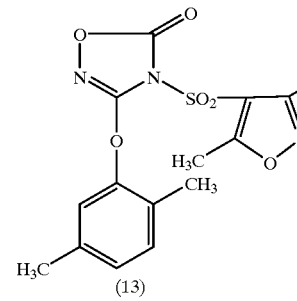 (13) | 50 | 94 |

TABLE A-continued
Phytophthora test (tomato)/protective
| Active compound | Application rate of active compound in g/ha | Efficacy in % |
|---|---|---|
| (14) | 50 | 96 |
| (16) | 50 | 95 |
| (17) | 50 | 95 |
| (18) | 50 | 96 |
| (19) | 50 | 95 |
| (22) | 50 | 91 |
| (23) | 50 | 99 |
What is claimed is:
1. A sulphonyloxadiazolone of the formula
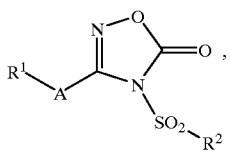
(I)
wherein A represents oxygen, sulphur, —SO—, —SO$_2$— or

where
R$^3$ represents hydrogen or an alkyl group,
R$^1$ represents an optionally substituted cycloalkyl group, an optionally substituted cycloalkenyl group or an optionally substituted aryl group and
R$^2$ represents an optionally substituted heterocyclic group.

2. The sulphonyloxadiazolone of formula (I) according to claim 1, wherein
A represents oxygen, sulphur, —SO—, —SO$_2$— or

R$^3$ represents hydrogen or an alkyl group having 1 to 4 carbon atoms,
R$^1$ represents a cycloalkenyl group having 3 to 8 carbon atoms or a cycloalkyl group having 3 to 8 carbon atoms which is optionally mono- to trisubstituted by identical or different substituents selected from the group consisting of halogen and an alkyl group having 1 to 3 carbon atoms or
R$^1$ represents an aryl group having 6 to 10 carbon atoms, where each of these radicals may be mono- to trisubstituted by identical or different substituents from the group consisting of
halogen, nitro, carbamoyl;
in each case, straight-chain or branched alkyl, alkoxy, alkylthio or alkylsulphonyl having in each case 1 to 6 carbon atoms;
in each case, straight-chain or branched alkenyl or alkenyloxy having in each case 2 to 6 carbon atoms;
in each case, straight-chain or branched halogenoalkyl, halogenoalkoxy, halogenoalkylthio or halogenoalkylsulphonyl having in each case 1 to 6 carbon atoms and 1 to 5 identical or different halogen atoms;
in each case, straight-chain or branched halogenoalkenyl or halogenoalkenyloxy having in each case 2 to 6 carbon atoms and 1 to 5 identical or different halogen atoms;
in each case, straight-chain or branched alkylamino, dialkylamino, alkylcarbonyl, alkoxycarbonyl, hydroximinoalkyl or alkoximinoalkyl having in each case 1 to 6 carbon atoms in the individual alkyl moieties;
in each case, doubly attached alkylene or dioxyalkylene having in each case 1 to 6 carbon atoms and being in each case optionally mono- to tetrasubstituted by identical or different substituents selected from the group consisting of halogen, straight-chain or branched alkyl having 1 to 4 carbon atoms and straight-chain or branched halogenoalkyl having 1 to 4 carbon atoms and 1 to 5 identical or different halogen atoms;
cycloalkyl having 3 to 6 carbon atoms; and/or
aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, where these aromatic or heterocyclic radicals may be mono- to trisubstituted by identical or different substituents selected from the group consisting of
halogen, nitro, straight-chain or branched alkyl having 1 to 4 carbon atoms,
straight-chain or branched halogenoalkyl having 1 to 4 carbon atoms and 1 to 5 identical or different halogen atoms,
straight-chain or branched alkoxy or alkylthio having 1 to 4 carbon atoms, and/or by straight-chain or branched halogenoalkoxy having 1 to 4 carbon atoms and 1 to 9 identical or different halogen atoms, and R$^2$ represents a heterocyclic radical having 5 or 6 ring members and 1 to 3 heteroatoms, where this radical may be mono- to trisubstituted by identical or different substituents selected from the group consisting of halogen, cyano, nitro, amino, hydroxyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxyl having 1 to 4 carbon atoms and 1 to 5 identical or different halogen atoms, alkylcarbonyl having 1 to 4 carbon atoms in the alkyl moiety, alkoxycarbonyl having 1 to 3 carbon atoms in the alkoxyl moiety, carbamoyl, alkylaminocarbonyl having 1 to 4 carbon atoms in the alkyl moiety, dialkylaminocarbonyl having 1 to 4 carbon atoms in the individual alkyl moieties, hydroximinoalkyl or alkoximinoalkyl having in each case 1 to 4 carbon atoms in the individual alkyl moieties and cycloalkyl having 3 to 6 carbon atoms.

3. A process for preparing a sulphonyloxadiazolone of the formula (I) according to claim 1 comprising reacting an oxadiazolone of the formula

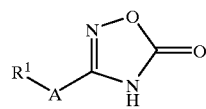

(II)

wherein
A and R$^1$ are as defined above,
with a sulphonyl halide of the formula

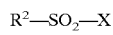

R$^2$—SO$_2$—X   (III)

wherein
R$^2$ is as defined above and
X represents halogen,
optionally, in the presence of an acid binder and optionally, in the presence of a diluent.

4. A microbicidal composition comprising a microbicidally effective amount of at least one sulphonyloxadiazolone of the formula (I) according to claim 1, an extender and/or a surfactant.

5. A method for controlling undesirable microorganisms in crops and in the protection of materials comprising applying a microbicidally effective amount of a sulphonyloxadiazolone of the formula (I) according to claim 1 to the microorganisms and/or their habitat.

6. A sulphonyloxadiazolone according to claim 1, characterized by the formula

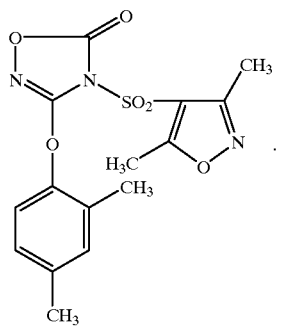

7. A sulphonyloxadiazolone according to claim 1, characterized by the formula

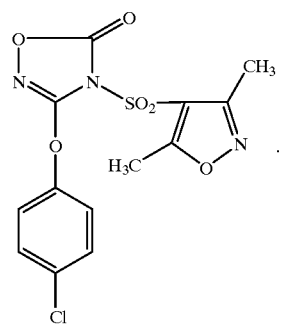

8. A sulphonyloxadiazolone according to claim 1, characterized by the formula

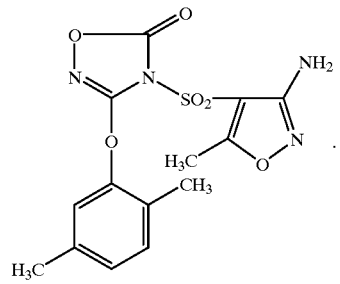

* * * * *